United States Patent
Delianides et al.

(10) Patent No.: US 8,632,262 B2
(45) Date of Patent: Jan. 21, 2014

(54) LASER TO FIBER OPTICAL COUPLING IN PHOTOPLETHYSMOGRAPHY

(75) Inventors: Theodore Philip Delianides, Boulder, CO (US); Jonas Alexander Pologe, Boulder, CO (US)

(73) Assignee: Kestrel Labs, Inc., Boulder, CO (US)

( * ) Notice: Subject to any disclaimer, the term of this patent is extended or adjusted under 35 U.S.C. 154(b) by 74 days.

(21) Appl. No.: 13/221,516

(22) Filed: Aug. 30, 2011

(65) Prior Publication Data
US 2013/0053662 A1    Feb. 28, 2013

(51) Int. Cl.
*G02B 6/36*    (2006.01)

(52) U.S. Cl.
USPC ............... 385/88; 600/323; 29/428; 385/90; 385/25

(58) Field of Classification Search
USPC ............... 385/88–94, 25; 600/323; 29/428
See application file for complete search history.

(56) References Cited

U.S. PATENT DOCUMENTS

| | | | |
|---|---|---|---|
| 4,296,998 A | 10/1981 | Dufft | |
| 4,690,492 A | 9/1987 | Beard | |
| 5,163,113 A | 11/1992 | Melman | |
| 5,351,329 A * | 9/1994 | Moore et al. | 385/92 |
| 5,692,086 A * | 11/1997 | Beranek et al. | 385/94 |
| 5,790,729 A | 8/1998 | Pologe | |
| 5,891,022 A | 4/1999 | Pologe | |
| 6,075,914 A * | 6/2000 | Yeandle | 385/49 |
| 6,190,056 B1 * | 2/2001 | Kwon et al. | 385/91 |
| 6,244,755 B1 * | 6/2001 | Joyce et al. | 385/90 |
| 6,253,097 B1 | 6/2001 | Aronow | |
| 6,364,543 B1 | 4/2002 | Fairchild | |
| 6,454,466 B1 * | 9/2002 | Weigel et al. | 385/80 |
| 6,597,843 B2 | 7/2003 | Johnson | |
| 6,647,279 B2 | 11/2003 | Pologe | |
| 6,754,515 B1 * | 6/2004 | Pologe | 600/322 |
| 6,910,811 B2 * | 6/2005 | Amorim | 385/90 |
| 7,194,167 B2 | 3/2007 | Barbarossa | |
| 7,477,810 B2 | 1/2009 | Miyokawa | |

* cited by examiner

Primary Examiner — Ellen Kim (57) ABSTRACT

An embodiment of a laser to fiber coupling apparatus having a substrate 110 that supports a laser mount 120, to which is affixed a submount 130 and laser die 140, and an open slot mount 150, in which a light guide 160 is affixed with an adhesive 170, such that the light from the laser 140 is coupled into the light guide 160. The open slot arrangement permits the light guide to be moved in all six translational and rotational degrees of freedom to maximally couple the light from the laser to the light guide. Other embodiments are described and shown.

18 Claims, 5 Drawing Sheets

LASER TO FIBER OPTICAL COUPLING IN PHOTOPLETHYSMOGRAPHY

STATEMENT REGARDING FEDERALLY SPONSORED RESEARCH OR DEVELOPMENT

This invention was made with government support under R44 HL073518 awarded by the National Institutes of Health. The government has certain rights in the invention.

BACKGROUND

Prior Art

U.S. Patents

| Pat. No. | Kind Code | Issue Date | Patentee |
|---|---|---|---|
| 4,296,998 | | Oct. 27, 1981 | Dufft |
| 4,690,492 | | Sep. 1, 1987 | Beard |
| 5,163,113 | | Nov. 10, 1992 | Melman |
| 5,790,729 | | Aug. 4, 1998 | Pologe |
| 5,891,022 | | Apr. 6, 1999 | Pologe |
| 6,253,097 | B1 | Jun. 26, 2001 | Aronow |
| 6,364,543 | B1 | Apr. 2, 2002 | Fairchild |
| 6,597,843 | B2 | Jul. 22, 2003 | Johnson |
| 6,647,279 | B2 | Nov. 11, 2003 | Pologe |
| 7,194,167 | B2 | Mar. 20, 2007 | Barbarossa |
| 7,477,810 | B2 | Jan. 13, 2009 | Miyokawa |

BACKGROUND OF THE INVENTION

In the science of photoplethysmography, light is used to illuminate or trans-illuminate living tissue for the purpose of providing noninvasive measurements of blood analytes or other hemodynamic parameters or tissue properties. In this monitoring modality light is directed into living tissue (the so-called "tissue-under-test") and a portion of the light which is not absorbed by the tissues, or scattered in some other direction, is detected a short distance from the point at which the light entered the tissue. The detected pulsatile photoplethysmographic signals are converted into electronic signals that are used to calculate blood analyte levels such as arterial blood oxygen saturation and/or hemodynamic variables such as heart rate, cardiac output, or tissue perfusion. A device which detects and processes photoplethysmographic signals to measure the levels of various blood analytes and/or various hemodynamic parameters is referred to as a photoplethysmographic measurement apparatus, photoplethysmographic device, or photoplethysmographic instrument. The first widespread commercially-used photoplethysmographic device in medicine was the pulse oximeter, a photoplethysmographic device designed to measure arterial blood oxygen saturation.

The introduction of laser light sources to photoplethysmography provides the opportunity to expand the field from the measurement of one blood analyte, specifically oxygen saturation, to the measurement of multiple blood analytes and physiological parameters. The narrow spectral bandwidth of laser light improves the spectral resolution, accuracy, and precision of photoplethysmographic measurements, thus making technically feasible the accurate measurement of analytes such as oxyhemoglobin, carboxyhemoglobin, methemoglobin, and reduced hemoglobin. Use of a photoplethysmographic instrument requires that light from each emitter (each light band) is incident on the tissue-under-test. When using one or more lasers as light sources in a photoplethysmographic device, the lasers often cannot be placed in the sensor that is positioned in close proximity to, or directly on, the tissue-under-test, as has been typical with LED-based photoplethysmographic sensors. This might be due to the physical size of the laser device being too large for placement in a conventional finger sensor, or because of the need to position the laser in close proximity to its driver electronics or thermal control components.

Regardless of exactly where the lasers are housed, if they are not at the sensor, the light emitted by the laser (or lasers) must be transmitted from the laser housing to the tissue-under-test, and this is typically accomplished by employing one or more light guides. The light guide may be any one of a number of elements, or a chain of elements, including optical elements such as glass or plastic optical fibers, liquid filled tubes, fiber optic bundles, or other light pipes.

The use of lasers in photoplethysmography was originally proposed nearly two decades ago; however, no laser-based photoplethysmographic monitors have yet been made commercially available. At least part of the reason for the delay in the commercial introduction of laser-based photoplethysmography are the unique challenges of how to create a low cost, high coupling efficiency, and minimal manufacturing complexity solution for coupling laser light into a light guide for transmission to the tissue-under-test.

Low cost and reduced manufacturing complexity are both achieved in part by using the simplest coupling method with minimal additional parts. A high coupling efficiency allows the use of lower power lasers to achieve the power out of the light guide, which further reduces system cost because laser cost tends to increase with increasing laser power. To maximize coupling efficiency, the ideal coupling method would allow movement of the light guide relative to the laser over all six independent degrees of freedom (three translational motions and three rotationally movements) to allow maximum light intensity to be launch into the light guide from the laser.

Photoplethysmography devices, namely pulse oximeter monitors, are also considered a low to medium volume item to manufacture. It is not as easy for manufacturers to amortize their manufacturing expenses if there are alignment and assembly steps that require capital-intensive manufacturing equipment or an inordinate amount of assembly time.

In fields other than photoplethysmography, the coupling of laser light to a fiber (or other types of light guides) typically includes the use of intervening optics such as ball lenses, cylindrical lenses, polarization maintaining optics, and optical feedback isolators which increases component count and introduces other opto-mechanical constraints that make such methods expensive and sensitive to misalignment. A low cost, low complexity, and versatile solution for laser to fiber coupling is thus still lacking for use in the field of photoplethysmography.

The use of fiber-coupled lasers in photoplethysmography is discussed in U.S. Pat. No. 6,253,097 and U.S. Pat. No. 6,647,279. These two patents disclose an apparatus consisting of a housing with one or more lasers each coupled to a fiber (see FIG. 12 of U.S. Pat. No. 6,253,097 and FIG. 1 of U.S. Pat. No. 6,647,279), but no details are provided regarding how the fiber and laser are mounted, aligned, or coupled. For example, U.S. Pat. No. 6,647,279 states "the emitters housed in the instrument are contained in the Laser Module 14. This module contains a set of laser diodes that are coupled into a fiber, a fiber bundle, or some other type of light guide 16, for transmission to the sensor and on to the tissue-under-test." There is no further disclosure of how each fiber is coupled to its respective laser.

U.S. Pat. No. 5,891,022 discloses "an emitter module 18 having a plurality of emitters 20, each capable of producing a light signal having a unique spectral content; a plurality of optical cables 21 each coupled to a single emitter source for carrying the corresponding light signal . . . " but provides no further disclosure of the manner in which the fibers are coupled to the emitters. In FIG. 3 of U.S. Pat. No. 5,891,022 is seen an apparatus of lasers, fiber connectors, and passive alignment coupling bodies wherein "The device mounts 44 are each adapted to receive a single laser diode 42 and to align the diode with a multimode connector 50 in the coupler unit 46." This type of "passive alignment" requires high precision and typically expensive opto-mechanical components to obtain reasonable coupling efficiency and effectively offers no degrees of freedom for movement of the fiber relative to the laser to maximize optical throughput. Alternatively one could use a large core optical fiber but this creates issues with patient cable design because large core fibers are less flexible and less durable.

Another laser to fiber coupling apparatus for a photoplethysmographic device is disclosed in U.S. Pat. No. 5,790,729 where a multimode optical coupler based on a planar waveguide is inserted between the emitters and the optical fibers. In this implementation the lasers, the multimode optical coupler, and the fibers must be accurately aligned to obtain reasonable optical throughput, and the use of the multimode optical coupler imposes additional optical throughput losses. The design and manufacture of these types of planar waveguide devices can also introduce significant non-recurring engineering (NRE) expenses.

Outside of the field of photoplethysmography, U.S. Pat. No. 4,690,492 discloses an emitter-to-fiber coupling apparatus intended for a catheter-based system. This invention uses a moveable bracket, shown in FIG. 4 of U.S. Pat. No. 4,690,492, to adjust the position of a light emitting diode (LED) emitter relative to the entrance face of a fiber held in a fixed position in a hole in the housing, stating "The brackets, which are fixed at one end, are constructed of thin flexible material so that the diodes can each be adjusted generally in the plane of the receiving end faces of the optical fibers . . . ". The inventor further states "By adjusting the free ends of the brackets each of the diodes can be precisely aligned with its associated light guide to provide maximum light energy transfer there between." Such an apparatus only allows for movement of the LED emitter in two degrees of freedom, both transverse to the optical axis, and relies on the fact that the emission pattern of an LED is fairly broad and uniform, making the coupling between the emitter and fiber more insensitive to misalignments. This is not the case for laser diodes, which have a tightly-constrained emission point and smaller angular emission pattern. In addition to the added cost of the brackets and related hardware, the apparatus disclosed in U.S. Pat. No. 4,690,492 has the added requirement that because the emitter is being moved, and not the optical fiber, its electrical leads must also be able to move in relation to the housing or an attached printed circuit board. This is not convenient for assembly or miniaturization of the packaging. And finally, the apparatus of U.S. Pat. No. 4,690,492 does not allow the emitter to be held in close thermal contact with the remainder of the housing. This is an important requirement for a laser-based photoplethysmographic device, where maintaining the temperature of the laser diode helps keep its center wavelength from shifting due to changing environmental conditions.

Completely outside of the field of the biological sciences and, more specifically, outside of the field of photoplethysmography, there are disclosed various apparatuses and methods for fiber coupling to lasers and other components, primarily for use in the telecommunications industry and related fields.

U.S. Pat. No. 6,364,543 discloses an apparatus where a clip or ferrule is used to hold the fiber along with numerous coupling optics, and the pre-fabricated assembly is positioned in front of the laser. This apparatus is inherently expensive in design and requires multiple manufacturing and process steps, including metallization, polishing, and gluing.

U.S. Pat. No. 7,194,167 discloses a pivot system for optically coupling a fiber to "optical components, such as filters, interferometers, beam splitters, etc. within optical fiber communications systems" but does not specifically mention lasers or other types of emitters. U.S. Pat. No. 6,597,843 discloses another embodiment of a fiber pivot apparatus and discusses its use for coupling a fiber to a laser emitter. Both U.S. Pat. No. 7,194,167 and U.S. Pat. No. 6,597,843 apparatuses, however, require multiple mechanical parts and have limitations on the degrees of freedom of the fiber movement, because of the pivoting nature of the alignment methods. In both cases the two translational axes of the fiber that are transverse to the primary optical axis are coupled to corresponding pitch and yaw rotational degrees of freedom. For example, a desired transverse movement in the horizontal X-direction can only be created if the fiber is rotated, or yawed, about the vertical Y-axis. Thus in this design there is an inherent limit in the independence of the degrees of freedom of movement of the fiber. The optical fiber is also always in contact with the pivot point. As seen in FIGS. 5 and 14 of U.S. Pat. No. 6,597,843, the v-groove contacts the fiber (or the rigid bulbous feature that has been added to the fiber, as seen in FIGS. 8 and 13 of U.S. Pat. No. 6,597,843) at all times while the fiber position is being adjusted. This means that there is only one orientation where the fiber axis is parallel to the primary optical axis of the laser emitter.

In U.S. Pat. No. 5,163,113 is seen a laser to fiber coupling apparatus that attempts to eliminate certain fiber alignment steps by using a grooved substrate to pre-align the fiber in relationship to the laser. This type of apparatus requires very precise placement of the laser chip and grooved substrate on the base substrate which could be accomplished by the design and manufacture of a so-called Silicon optical bench. Such optical benches have a high initial non-recurring engineering (NRE) cost to achieve sufficient feature tolerances for placing the laser and fiber components using passive alignment techniques. They also allow limited flexibility in the emitters that can be used with a specific optical bench, once designed, because the exact size of the laser die and the location of light emission from the front of the laser die can vary greatly from one manufacturer to another. This is a significant problem in photoplethysmography because the wide range of laser wavelengths that can be required to make various analyte measurements may require the use of lasers from several different manufacturers in any one photoplethysmographic device. Such an approach may therefore be too expensive and inflexible for the comparatively low production volumes required for photoplethysmography.

U.S. Pat. No. 4,296,998 and U.S. Pat. No. 7,477,810 both disclose a method for mounting an optical fiber in front of a laser diode where the fiber is placed within a drop of solder placed on a flat pedestal. The use of solder requires that the fiber exterior and the pedestal first be metalized with gold, which adds additional manufacturing steps and cost. Melting the solder requires the precise placement of heat, otherwise the semiconductor laser diode could be destroyed, given the typical melting temperatures of even a low-temperature solder. Furthermore, claim 4 of U.S. Pat. No. 4,296,998 describes the method of using laser light to melt the solder, which means that an additional piece of expensive capital equipment must be used in the manufacturing process.

U.S. Pat. No. 7,477,810 further discloses that the drop of solder could be replaced with an adhesive or synthetic resin, so that "an optical fiber of which external periphery is not metal-coated may also be used." This embodiment loses the advantage of having the molten solder held in place by the location of the metalized surfaces, in the same manner that the flow of solder is controlled on a printed circuit board during assembly. If the solder is replaced with a drop of adhesive, the adhesive will migrate onto any available surfaces, potentially even including the sides of the flat pedestal. It will possibly sag and flow away from the fiber rather than encircling the fiber. This problem is further exacerbated if heat is introduced during the curing of the adhesive, which reduces the viscosity of the adhesive. This heat could be introduced either because of an elevated temperature cure or as a side effect of using a curing ultraviolet light. Additionally, positioning the fiber above the pedestal, with the adhesive placed between the two, introduces the possibility of fiber misalignment due to shrinkage of the adhesive during its cure, which would pull the fiber towards the pedestal. This design is more suitable for positioning the fiber with a small amount of adhesive directly against the pedestal in a passive alignment scheme. It is less suitable for an application where it is desirable to perform an active alignment and fixation of the light guide in front of a laser whose light emission location could vary widely.

One other problematic issue with all of the aforementioned non-photoplethysmography-related inventions for laser to fiber coupling is that the lasers are handled and mounted only in die or chip form (possibly including a small heat-spreader submount). The assembly thus requires precision pick-and-place die bonding and subsequent wire bonding of these microscopic elements onto the apparatus, which introduces the need for additional expensive capital equipment for the assembly process.

None of the previously discussed apparatuses are well suited for laser to fiber coupling for use in the field of photoplethysmography, and this is one of the reasons that there are currently no laser-based photoplethysmographic devices in clinical use. The ideal apparatus would have a minimum of parts to reduce cost and size, have minimal thermal mass, and work with a variety of laser types, thus allowing it to be easily incorporated into various types of photoplethysmographic devices. Because cost is driven not only by the complexity of the apparatus but also by the methods used for assembly manufacturing, it is important that the fiber-coupled laser apparatus not require capital-intensive processing and alignment systems and that its construction not require an inordinate amount of assembly time. The apparatus should ideally be buildable with small core diameter light guides, to allow the creation of patient cables that have high flexibility. Furthermore, it would be advantageous to be able to work with laser diodes that have already been mounted on inexpensive pre-packaged headers such as the "TO" family of optoelectronics packages (e.g. TO-5, TO-18, TO-46, etc.). Therefore, the need exists for a small, low-cost, actively-aligned apparatus which accurately and securely holds a light guide in position to align its end face for efficient coupling of light emitted from a laser.

BRIEF SUMMARY OF THE INVENTION

In accordance with one embodiment an optics module for a photoplethysmographic device comprises a substrate with at least one light guide conducting light from a laser wherein the light guide is affixed within an open slot attached to the same substrate as the laser. The optics module can be comprised of a plurality of these laser to fiber coupling pairs, all mounted on a common substrate to allow further mounting to a thermally-controlled element to permit precise control over the temperature of the lasing elements. Accordingly, several advantages of one or more aspects are as follows: the apparatus will accept a wide range of laser and light guide types and sizes; the light guide can be mounted in any combination of translational and rotational positions; there is high optical coupling efficiency between each laser and light guide. The combination of these advantages contributes to the ability to build a laser-based photoplethysmographic device.

DETAILED DESCRIPTION OF THE INVENTION

Figure 1:
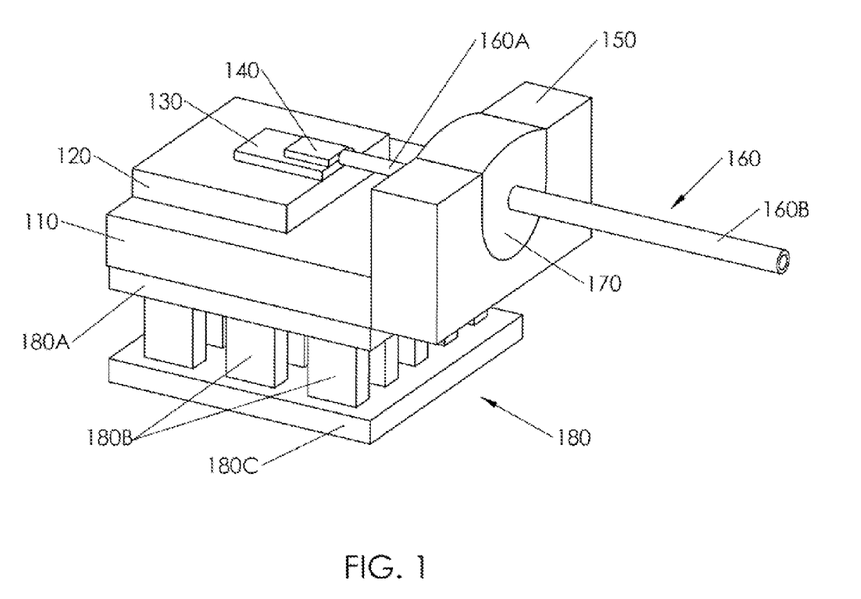
FIG. 1. Laser to fiber coupling apparatus.

One embodiment of a laser to fiber coupling apparatus for a laser-based photoplethysmographic device is shown in isometric view in FIG. 1. A substrate 110 supports a laser 140 on a mechanical mount 120. The laser 140 may also be affixed to a submount 130 before being mounted on mechanical mount 120. Substrate 110 also supports a second mechanical mount 150 with an open slot that holds an adhesive 170 to support a light guide 160 in a fixed position in front of the laser 140. The entire substrate 110 is mounted to the device side 180A of a thermoelectric (TE) cooler (or TEC) 180 that is also comprised of a plurality of semiconductor junctions 180B and a heat sink side 180C.

Figure 5:
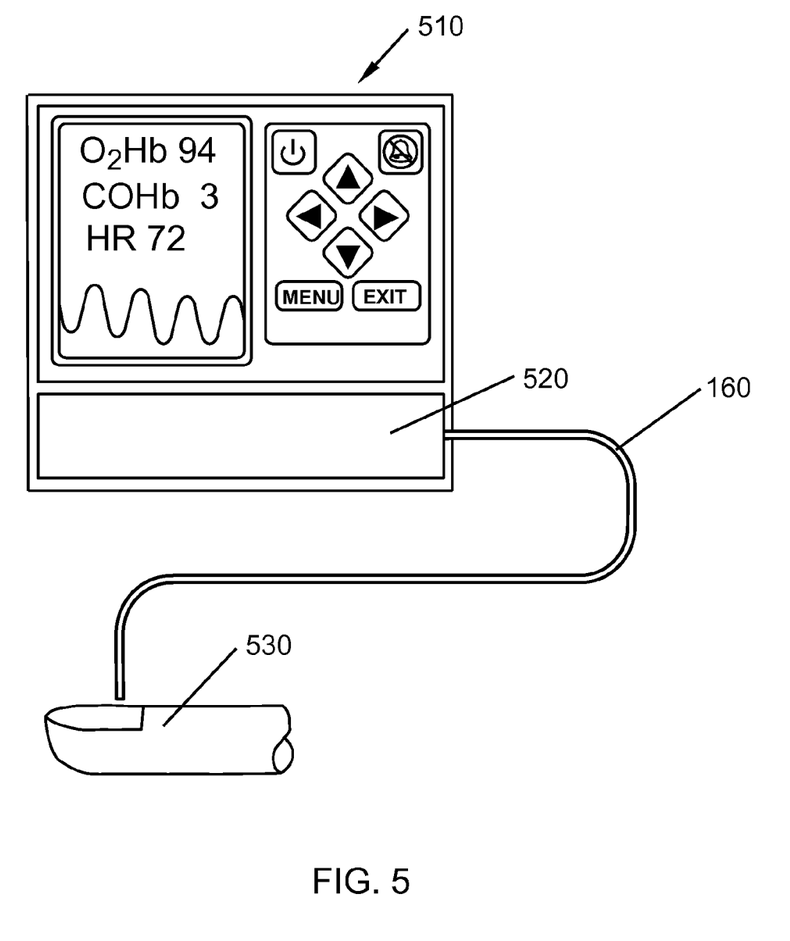
FIG. 5. Laser-based photoplethysmographic device with optics module and light guide.

The apparatus of FIG. 1 provides a simple, low-cost means to couple light from a laser 140 onto a light guide 160 for delivery to the tissue-under-test 530 and is the basis for an optics module 520 in a laser-based photoplethysmographic device 510. The laser 140 shown is in semiconductor die or chip form and typically is mounted on a submount 130. Although the laser 140 can be mounted directly onto the laser mount 120, the submount can serve several useful purposes. It can have a larger physical size (than the laser) for ease of handling and it can provide a high thermal conductivity interface to help move heat away from the laser semiconductor junction. It may also provide electrical connection to the laser. The mechanical mount 120 that holds the laser 140 and possibly a laser submount 130 is rigidly attached to the substrate 110. The mechanical mount 120 is rigidly held in position on, to, or as part of the substrate 110 and in close proximity to a second mechanical mount 150 that includes an open slot. Although in this embodiment the substrate 110 and the pair of mechanical mounts (laser mount 120 and open slot mechanical mount 150) are shown as three separate parts, any two or all three can be made from one machined, molded, or stamped part, for ease of manufacture. Additionally, either the substrate 110 or the laser mount 120 can provide space for mounting, if required, other components such as a monitoring photodiode or a thermistor used to monitor the temperature of the assembly, to provide feedback to control circuitry that is driving the TE cooler 180. The substrate and any one or both of the mechanical mounts can also be part of an overall housing or case for the optics module.

The apparatus in FIG. 1 is shown with a laser light source, although other types of light sources could be used, including, for example, light emitting diodes, tungsten or other filament type lamps, or gas lamps. The laser could be a semiconductor laser, a gas laser, a dye laser, or nearly any other type of laser where the laser light can be directed or launched into a light guide 160.

The light guide 160 is mounted using a second mechanical mount 150, which can also be referred to as an open slot mechanical mount because of the inclusion of a slot, groove, or saddle feature within the mount. This open slot feature can also be machined, molded, stamped, or otherwise built directly into the substrate 110 if the second mechanical mount is integral to the substrate. The light guide 160 could be any of a number of different elements that conduct light from one point to another including glass or plastic optical fibers, liquid light guides, plastic light pipes, or other such elements. In the case of an optical fiber, the light guide would typically include a core and cladding as well as possibly a protective buffer, coating, or jacket, which provides durability during handling and processing steps. The entrance face of the light guide would already be prepared with any stripping, cleaving, polishing, and anti-reflection or filter coating steps completed prior to the light guide being mounted in the apparatus. Likewise, the entrance face of the light guide could be flat, angled, lensed, or otherwise shaped to optimize optical performance. Unlike other apparatuses for laser to fiber coupling, in this design there is no requirement that the fiber be pre-mounted in a ferrule or holder or that any other optical elements be pre-aligned in the system.

Mounting of the light guide 160 within the open slot mechanical mount 150 is achieved using an adhesive 170. The adhesive could be any material that provides the required fixation of the light guide within the open slot, including epoxies, acrylics, and glues, and it could be either a thermoplastic material or a thermoset, two-part chemical, or UV cure material. Use of an adhesive that can be cured to a rigid state by illumination with ultraviolet light provides the added advantage that it can greatly reduce the time required for assembly. The adhesive 170 could also be replaced with a solder if the exterior of the light guide 160 is gold metalized in the region where it passes through the open slot, the interior of which would also be gold metalized. The most important requirement is that the cured or set adhesive or solder affix the light guide 160 in place within the open slot 150 after the light guide has been coupled to the laser source 140.

In FIG. 1 only a short segment of the light guide 160 is shown, but in actual implementation it would be long enough to reach either a connector or other optical element that is part of the optical path for delivering light to the tissue-under-test. The entire apparatus could be placed inside a housing (which could also serve to conduct heat from the heat sink side 180C of the TE cooler 180 to an external heat sink), to protect it from physical damage or from exposure to changing environmental conditions, in which case appropriate features would be included in the housing to allow the pass through of the light guide 160 and of electrical contacts to, for example, the laser, thermoelectric cooler, and thermistor. As mentioned previously, any combination of the various substrate, mechanical mount, and open slot features could be machined, molded, or stamped directly into the housing to save cost and weight and to eliminate assembly steps.

Figure 2A:
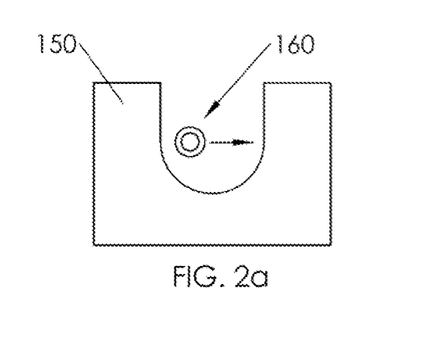
FIG. 2a. Horizontal movement (translation along x-axis) of light guide within an open slot.
Figure 2B:
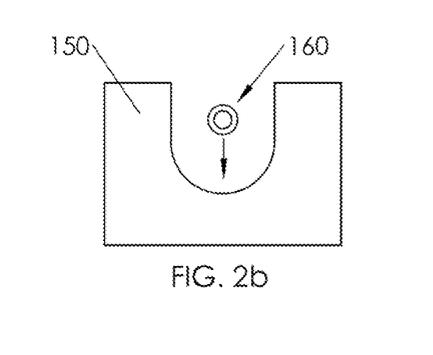
FIG. 2b. Vertical movement (translation along y-axis) of light guide within an open slot.
Figure 2C:
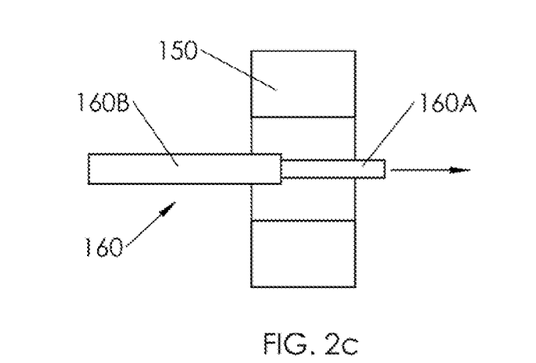
FIG. 2c. Optical axis movement (translation along z-axis) of light guide within an open slot.
Figure 2D:
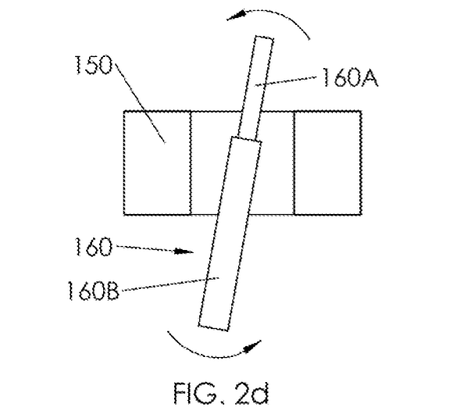
FIG. 2d. Yawing movement (rotation about y-axis) of light guide within an open slot.
Figure 2E:
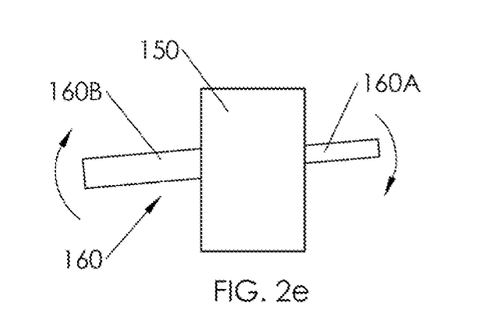
FIG. 2e. Pitching movement (rotation about x-axis) of light guide within an open slot.
Figure 2F:
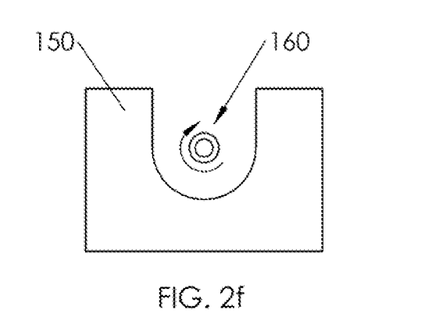
FIG. 2f. Rolling movement (rotation about z-axis) of light guide within an open slot.

A key advantage of this optical module in general and the laser to fiber coupling it enables is provided by the use of an open slot to hold the light guide. By using an open slot that is larger than the diameter of the light guide, the light guide can be easily moved in all directions with six degrees of freedom until the light from the laser that has been launched into the light guide has been maximized. The light guide 160 does not need to make contact with the open slot of the second mechanical mount 150 but can still be held rigidly within the slot by filling the remaining space with an adhesive 170 and curing the adhesive to a rigid state after light guide alignment. The order of the assembly steps of aligning the light guide and adding the adhesive (before it is cured to a rigid state) can also be reversed. Having six degrees of freedom of movement, as shown in FIG. 2 where the light guide 160 is being positioned inside the open slot 150, means that translation can occur along three orthogonal axes (FIGS. 2A, 2B, and 2C, showing translation along the X-, Y-, and Z-axes) and independent rotation can also be performed about these same three axes (FIGS. 2D, 2E, and 2F, showing rotation about the X-, Y-, and Z-axes, also termed pitch, yaw, and roll).

Having this level of positional flexibility provides a useful improvement to methods of light guide coupling that have limited degrees of freedom of movement. The light guide can be placed in a wide range of positions and orientations to reach a laser output location that is not well defined prior to apparatus construction or repeatable from one laser manufacturer to another. There is also almost no limit to the size or type of light guide that can be used, as long as the open slot is properly sized. The open slot also provides other advantages. It supports the adhesive from multiple directions, providing a capture well for the adhesive when it is applied, to prevent it from flowing or sagging away from the desired location. Capillary action due to surface tension and the presence of sharp corner edges around the periphery of the open slot both help to restrain the uncured adhesive within the internal curve of the open slot, even when the light guide is being moved within the slot during positioning to maximize optical coupling from the laser.

Supporting the adhesive from multiple directions, i.e. confining it within the walls of the open slot, prevents the light guide from being pulled out of alignment if the adhesive shrinks when cured. Also, with an open slot the light guide can be picked up with a small microgripper manipulator very close to its entrance face, providing maximum rigidity during alignment, and placed in its final position with one series of motions. In the case of a passthrough mount hole, the light guide might have to be picked up and passed between two or more manipulators, introducing the possibility of damaging the end face or an optical coating added to the end face, of the light guide while it is being passed through the opening. The simplicity of the apparatus design eliminates the need for intervening optics and additional clips, brackets, ferrules, hold-down screws, and other mechanical parts that are seen in prior art apparatuses. It provides the simultaneous benefits of minimal part count with maximum freedom of movement of the light guide during optical coupling.

The light guide 160 may be an optical fiber 160A that is protected or jacketed by a buffer 160B, which could be an acrylate, polyimide, or other coating designed to protect the fiber during use. In this case it may be advantageous to remove a portion of the jacket such that the transition from buffered to unbuffered fiber occurs within the open slot, so that the bare fiber 160A partially protrudes from the buffer 160B. This would allow the application of the adhesive 170 so that it makes contact with the open slot, the fiber, and the buffer, fixing both the fiber and the buffer in position within the open slot. An advantage is gained because the exterior of an optical fiber light guide (the cladding) is more rigid than the softer buffer jacket, and bonding directly to this rigid surface provides maximum long-term stability of the fiber position in front of the laser. An additional bonding to the protective buffer provides strain relief distal to the coupling location, helping to prevent the fiber from breaking if it is flexed or otherwise bent during further processing steps.

Figure 3:
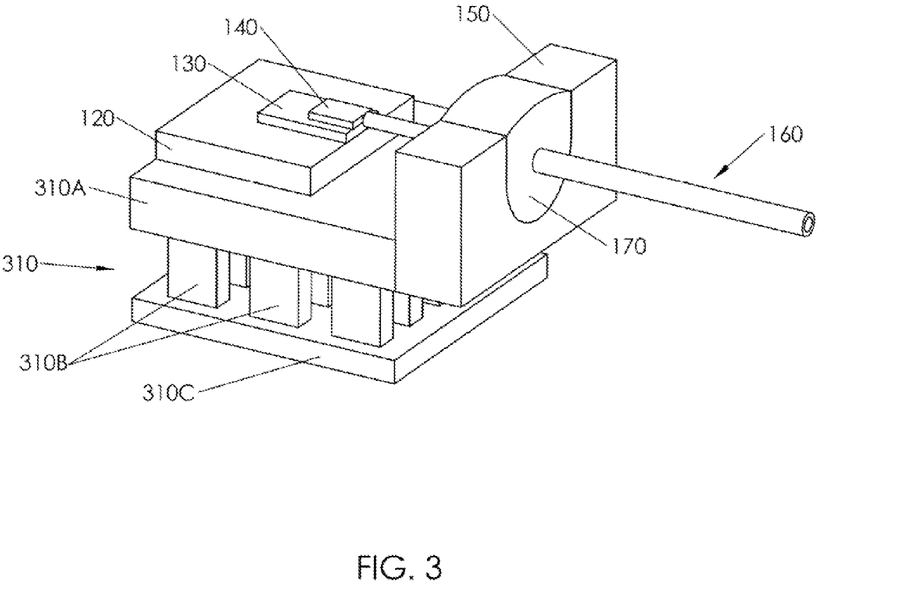
FIG. 3. Apparatus with substrate integral to device side of the thermoelectric cooler FIG. 4a. Apparatus with laser die mounted on standard TO-header.

In the embodiment of FIG. 1, the substrate 110 has a flat surface that allows it to be mounted with good thermal contact to the device side 180A of the TE cooler 180. An alternate embodiment is seen in FIG. 3, where the mount substrate (110 in FIG. 1) and the TEC device side (180A in FIG. 1) are combined into a single integral substrate 310A that forms the device side of the TE cooler 310. The TE cooler is also comprised of a plurality of semiconductor junctions 310B and a heat sink side 310C. This would further reduce the size and weight of the apparatus and also simplify the thermal conduction path from the laser 140 to the heat sink side 310C of the TEC. As has been discussed previously, one or both of the mechanical mounts could also be made integral to this integrated substrate 310A, to further reduce complexity and thermal resistance.

Figure 4A:
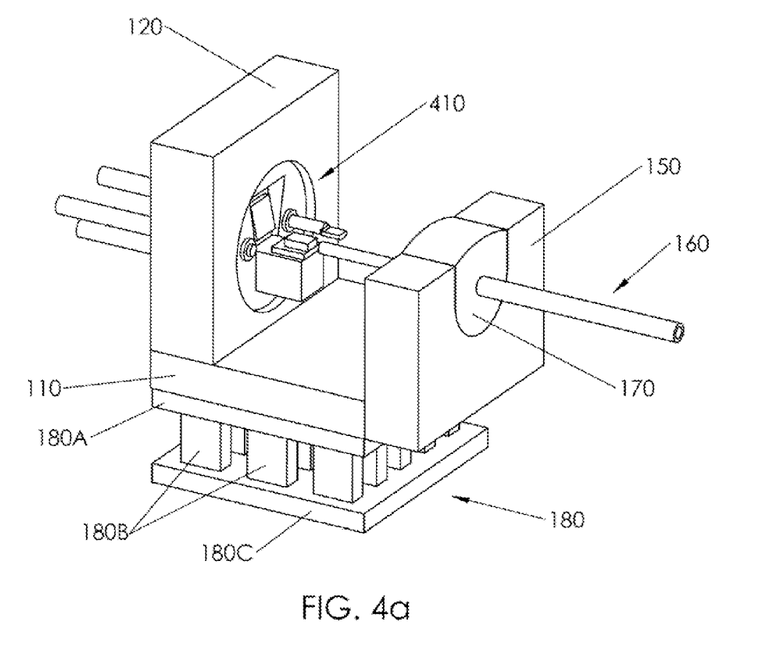
Figure 4B:
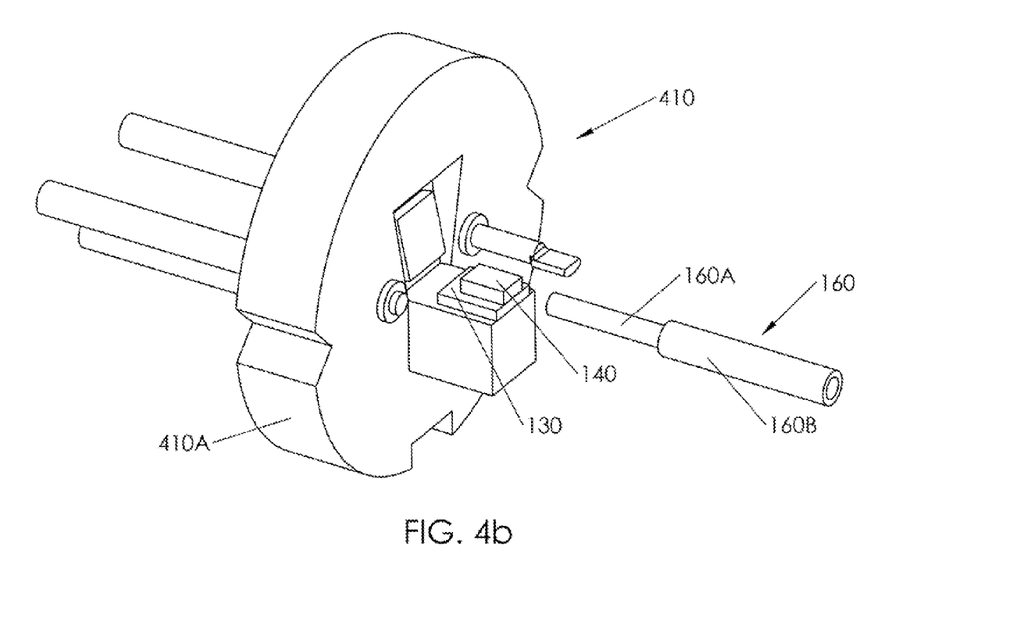
FIG. 4b. Close up of laser die mounted on standard TO-header and coupled to fiber.

Another embodiment of the laser to fiber coupling apparatus is shown in FIG. 4, which illustrates the versatility of this apparatus. Semiconductor diode lasers can come as loose die or already mounted on a submount or heat spreader, but they are also commonly purchased already pre-packaged on inexpensive "TO" headers such as the common TO-5, TO-18, and TO-46 optoelectronics packages. FIG. 4a shows an embodiment in which the substrate 110 holds a specially configured version of mechanical mount 120 and the open slot mount 150. Similar to previous embodiments, the substrate 110 is mounted to the device side 180A of the TE cooler 180. The laser mount 120 is specifically designed to hold a TO-packaged laser 410. The TO-packaged laser 410, shown in more detail in FIG. 4b, includes a base 410A, a submount 130, and a laser die 140. The laser base 410A can be rigidly attached to the laser mount 120 with adhesive, soldering, resistance welding, or other attachment means. As in previous embodiments, the light guide 160 is positioned within an open slot mechanical mount 150 and fixed in place with an adhesive 170. Given that the exact position of the laser die 140 could vary greatly between lasers of different wavelength and output power, as well as from one manufacturer to another, a distinct advantage is gained by being able to locate the light guide 160 in almost any position within the open slot 150 for efficient coupling to the laser 140. In a similar manner, additional embodiments could be constructed in which almost any type of light source could be similarly mounted and fiber coupled, including, for example, a Helium-Neon laser mounted in its housing tube or a large benchtop Xenon-Chloride excimer gas laser used for scientific research.

Any of the shown embodiments could also be configured into a multiplace apparatus to create a multi-wavelength optics module 520 for a photoplethysmographic measurement system 510. A multiplace configuration would include two or more pairs of mechanical mounts 120, 150 attached to one or more substrates 110 to create an optical module with two or more discrete laser light sources. As before, combining multiple pairs of mechanical mounts and their substrate (or substrates), including among multiple lasers, into one integrated package would further reduce the size, complexity, and cost of this optics module 520.

The previous discussion of the embodiments has been represented for the purposes of illustration and description. The description is not intended to limit the invention to the form disclosed herein. Variations and modifications commensurate with the above are considered to be within the scope of the present invention. The embodiments described herein are further intended to explain the best modes presently known of practicing the invention and to enable others skilled in the art to utilize the invention as such, or in other embodiments, and with the particular-modifications required by their particular application or uses of the invention. It is intended that the appended claims be construed to include alternative embodiments to the extent permitted by the prior art.

The invention claimed is:

1. A photoplethysmographic device including an optics module, the optics module comprising:
   a. a substrate having one or more pairs of mechanical mounts, each of the pairs of mechanical mounts comprised of a first mechanical mount and a second mechanical mount located in close proximity to the first mechanical mount;
   b. a light source affixed to the first mechanical mount;
   c. the second mechanical mount having an open slot formed therein designed to allow a light guide to be movably positioned in all translational and rotational axes within the open slot;
   d. the light guide affixed within the open slot in a position to substantially maximally couple light emitted by the light source into the light guide.

2. The apparatus of claim 1 wherein at least one of the light sources for each of the pairs of mechanical mounts is a laser.

3. The apparatus of claim 1 wherein the light guide is fixed in position within the open slot by an adhesive.

4. The apparatus of claim 3 wherein the adhesive is a light-curable adhesive.

5. The apparatus of claim 1 wherein
   the light guide is jacketed by a buffer,
   the light guide protrudes from the buffer, and
   both the light guide and the buffer are fixed in position within the open slot by an adhesive.

6. The apparatus of claim 5 wherein the adhesive is a light-curable adhesive.

7. The apparatus of claim 1 wherein the substrate is integral to one side of a thermoelectric cooler.

8. The apparatus of claim 1 wherein the substrate includes a substantially flat surface to allow the substrate to be mounted to one side of a thermoelectric cooler.

9. A photoplethysmographic device including an optics module, the optics module comprising:
   a. a substrate including a first mechanical mount and a second mechanical mount;
   b. a laser light source affixed to the first mechanical mount;
   c. the second mechanical mount including an open slot designed to allow a light guide to be movably positioned in all translational and rotational axes within the open slot;
   d. the light guide affixed with an adhesive within the open slot in a position that substantially maximally couples light emitted by the laser light source into the light guide.

10. A method for manufacturing an optics module in a photoplethysmographic measurement system comprising the steps of:
   a. providing a substrate containing a plurality of one or more pairs of mechanical mounts;
   b. providing a light source for each of the pairs of mechanical mounts;
   c. providing a light guide for each of the pairs of mechanical mounts;
   d. providing a first mechanical mount in each of the pairs of mechanical mounts;
   e. affixing the first mechanical mount on the substrate;
   f. affixing the light source to the first mechanical mount;
   g. providing a second mechanical mount in each of the pairs of mechanical mounts;
   h. affixing the second mechanical mount on the substrate in proximity to the first mechanical mount;
   i. providing an open slot in the second mechanical mount;
   j. aligning the light guide in the open slot to substantially maximally couple light, emitted by the light source held in the first mechanical mount, into the light guide;
   k. affixing the light guide into position in the open slot.

11. The method of claim 10 wherein the step of affixing the light guide in position includes the step of applying an adhesive that makes contact with both the light guide and the slot.

12. The method of claim 11 wherein the step of applying the adhesive includes applying a light-curable adhesive.

13. The method of claim 10 wherein the step of providing the light guide includes the additional step of providing a light guide that is partially surrounded by a buffer and the step of affixing the light guide in position includes the additional steps of removing a portion of the buffer and of applying an adhesive to make contact with the light guide, the buffer, and the open slot.

14. The method of claim 13 wherein the step of applying the adhesive includes applying a light-curable adhesive.

15. The method of claim 14 wherein the step of affixing the light guide into position includes illuminating the light-curable adhesive to cause curing of the light-curable adhesive to a substantially rigid state.

16. The method of claim 10 wherein the step of providing a substrate includes providing a substrate that is integral to one side of a thermoelectric cooler.

17. The method of claim 10 wherein the step providing a substrate includes providing a substrate with a substantially flat surface to allow the substrate to be mounted to one side of a thermoelectric cooler.

18. The method of claim 10 wherein the step of providing a light source comprises the step of providing a laser light source.

* * * * *